United States Patent [19]

McCarthy et al.

[11] Patent Number: 5,371,278
[45] Date of Patent: Dec. 6, 1994

[54] SYNTHESIS OF IOVERSOL USING A MINIMAL EXCESS OF ACETOXYACETYLCHLORIDE

[75] Inventors: William Z. McCarthy, St. Louis; Mills T. Kneller, University City; Youlin Lin, Chesterfield; Rebecca A. Wallace, Manchester; David H. White, Ballwin, all of Mo.

[73] Assignee: Mallinckrodt Medical PMC, Las Vegas, Nev.

[21] Appl. No.: 217,575

[22] Filed: Mar. 25, 1994

[51] Int. Cl.$^5$ .............................................. C07C 67/02
[52] U.S. Cl. .................................................... 560/251
[58] Field of Search .......................................... 560/251

[56] References Cited

U.S. PATENT DOCUMENTS 4,396,598  8/1983  Lin ........................................ 424/5

Primary Examiner—José G. Dees
Assistant Examiner—Joseph M. Conrad
Attorney, Agent, or Firm—Rita Downard Vacca

[57] ABSTRACT

The use of a minimal excess of acetoxyacetylchloride as a reagent in the synthesis of N,N'-bis(2,3-dihydroxypropyl)-5-N-(2-hydroxy-ethyl)glycolamido-2,4,6-triiodoisophthalamide.

29 Claims, No Drawings

SYNTHESIS OF IOVERSOL USING A MINIMAL EXCESS OF ACETOXYACETYLCHLORIDE

Field of the Invention

The present invention relates to the use of a minimal excess of acetoxyacetylchloride as a reagent in the synthesis of Ioversol.

BACKGROUND OF THE INVENTION

Ioversol is disclosed as a useful nonionic x-ray contrast agent in U.S. Pat. No. 4,396,598. 5-acetoxyacetamido-N,N'-bis(2,3-diacetoxypropyl)-2,4,6-triiodoisophthalamide having the following structure:

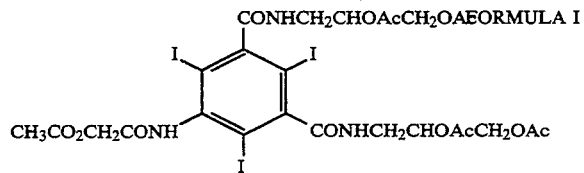

is an intermediate compound in the production of ioversol. The compound of Formula I and its use in the production of ioversol is likewise disclosed in U.S. Pat. No. 4,396,598 incorporated herein by reference. 5-acetoxyacetamido-N,N'-bis(2,3-diacetoxypropyl)-2,4,6-triiodoisophthalamide, as disclosed in U.S. Pat. No. 4,396,598, may be produced by adding acetoxyacetylchloride (AAC) to a N,N-dimethylacetamide and 1,1,2-trichloroethane solution of a compound of the following structure:

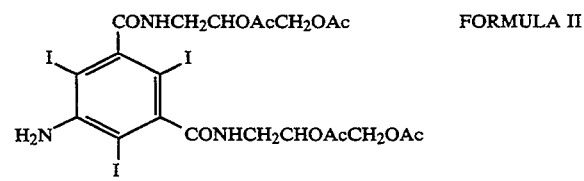

and stirring until the reaction is complete. The reaction mixture is then diluted with 1,1,2-trichloroethane and extracted with aqueous sodium bicarbonate solutions and aqueous sodium chloride solutions.

The dilution procedure using 1,1,2 trichloroethane may alternatively be carried out using an organic solvent such as, but not 1 limited to, carbon tetrachloride, dichloromethane, chloroform, 1,2-dichloroethane, 1,1,2-trichloroethylene, 1,1,2-trichloroethane, 1,1,1-trichloroethane and tetrachloroethylene, but most preferably 1,1,2trichloroethane.

The procedure for producing 5-acetooxyacetamido-N,N'-bis(2,3-diacetoxypropyl)-2,4,6-triiodoisophthalamide has become well known in the art and heretofore required the use of a 100% excess of acetoxyacetylchloride (AAC) to perform the intermediate synthetic step just described.

An improved procedure that minimizes the need for acetoxyacetylchloride (AAC) in the intermediate synthetic step which produces 5-acetoxyacetamido-N,N'-bis(2,3-diacetoxypropyl)-2,4,6-triiodoisophthalamide is desired as an alternate and more cost efficient method of producing ioversol. It is, therefore, an object of the present invention to meet these needs.

SUMMARY OF THE INVENTION

The present invention is a method of producing ioversol using only approximately 7 to 36%, but preferably a 12% excess, of acetoxyacetylchloride (AAC) as opposed to a 100% excess as taught by prior art. The procedure begins with a solvent solution of 5-amino-N,N'-bis(2,3-diacetoxypropyl)-2,4,6-triiodoisophthalamide(1). Compound 1 may be prepared for use in this reaction by distilling off some of the solvent to remove and/or reduce impurities, or alternatively, the solvent solution may be used directly without distillation. N,N-dimethylacetamide (DMAC) and acetoxyacetylchloride (AAC), are then added to between 1 to 3 grams, but preferably 1.72 grams, of 5-amino-N,N'bis(2,3-diacetoxypropyl)-2,4,6-triiodoisophthalamide (1) plus up to 5 milliliters, but preferably 1 milliliter of suitable solvent to form a highly concentrated solution. The concentrated solution is then stirred at a temperature within the range of 40° C. to 66° C. but preferably at the optimal temperature of 50° C., as opposed to the temperature of 37° C. taught by prior art, until the reaction is complete. Hydrochloric acid is produced as a waste product of this reaction. The DMAC present in the solution is mildly basic and thereby reacts with the hydrochloric acid generated to form a DMAC.HCl complex. After dilution with an organic solvent, the reaction solution is extracted with aqueous sodium bicarbonate solution(s) and aqueous sodium chloride solution (s) . The resulting 5-(acetoxyacetamido)-N,N'-bis(2,3-diacetoxypropyl)-2,4,6-triiodoisophthalamide(2) may be used without further purification as an intermediate in the production of N,N'-bis(2,3-dihydroxypropyl)-5-[N-(2-hydroxyethyl)-glycolamido]2,4,6-triiodoisophthalamide (ioversol) (4) according to the reactions illustrated in Scheme I below. The final product, ioversol (4), produced through the use of only a 12% excess of AAC, has an equivalent or increased purity, approximately 95%, as compared to that produced through the use of 100% excess AAC as previously believed necessary to reach such levels of purity.

SCHEME 1

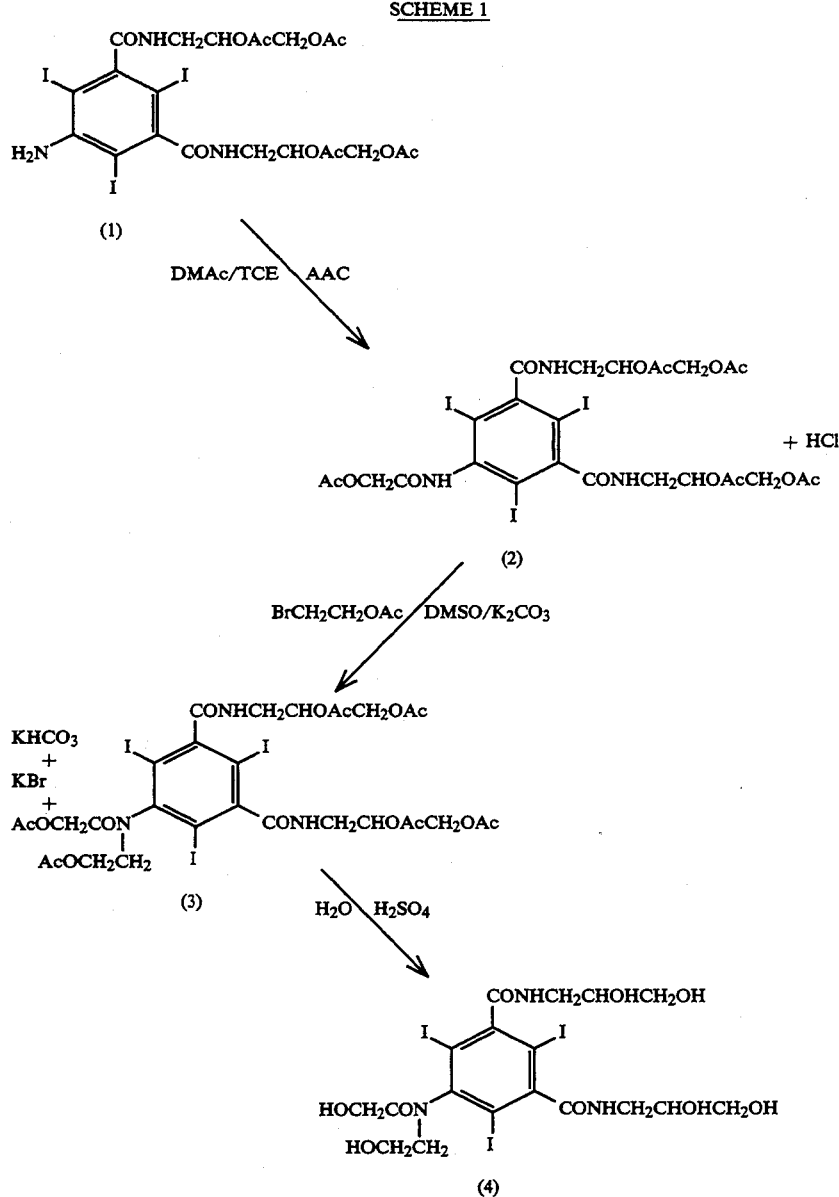

AAC = Acetoxyacetylchloride
DMAC = N,N-dimethylacetamide
TCE = 1,1,2-trichloroethane
DMSO = Dimethylsulfoxide Another method of producing ioversol according to the present invention using a minimal excess, such as 7 to 36% but preferably 12% acetoxyacetylchloride (AAC), uses dried 5-amino-N,N'bis(2,3-dihydroxypropyl)-2,4,6-triiodoisophthalamide (5) which normally serves as a precursor to 5-amino-N,N'bis(2,3-diacetoxypropyl)-2,4,6triiodoisophthalamide(1) in the ioversol process. Therefore, this particular method combines two reaction steps into one simplified reaction step, namely the production of 5-amino-N,N'-bis(2,3-diacetoxypropyl)-2,4,6triiodoisophthalamide(1), in the production of ioversol (4). This step-saving and time-saving method begins by adding N,N-dimethyl-acetamide (DMAC) and acetoxyacetylchloride (AAC) to 5-amino-N,N'-bis(2,3-dihydroxypropyl)-2,4,6triiodoisophthalamide (5) and stirring until the reaction is complete. (4-dimethyl-aminopyridine (DMAP) may also be used as a catalyst and added to compound (5) along with the DMAC and AAC although it is not necessary.) Hydrochloric acid is produced as a waste product of this reaction. After dilution with an organic solvent, the reaction solution is extracted with aqueous sodium bicarbonate solution(s) and aqueous sodium chloride solution(s). The resulting pentaacetate-derivative of 5-acetoxyacetamido-N,N'-bis(2,3-diacetoxypropyl)-2,4,6 -triiodoisophthalamide(6) may be used without further purification in the production of N,N'-bis(2,3-dihydroxypropyl)-5-[N-(2-hydroxyethyl)-glycolamido]-2,4,6-triiodoisophthalamide (ioversol) (4) according to the reactions illustrated in Scheme 2 below.

SCHEME 2

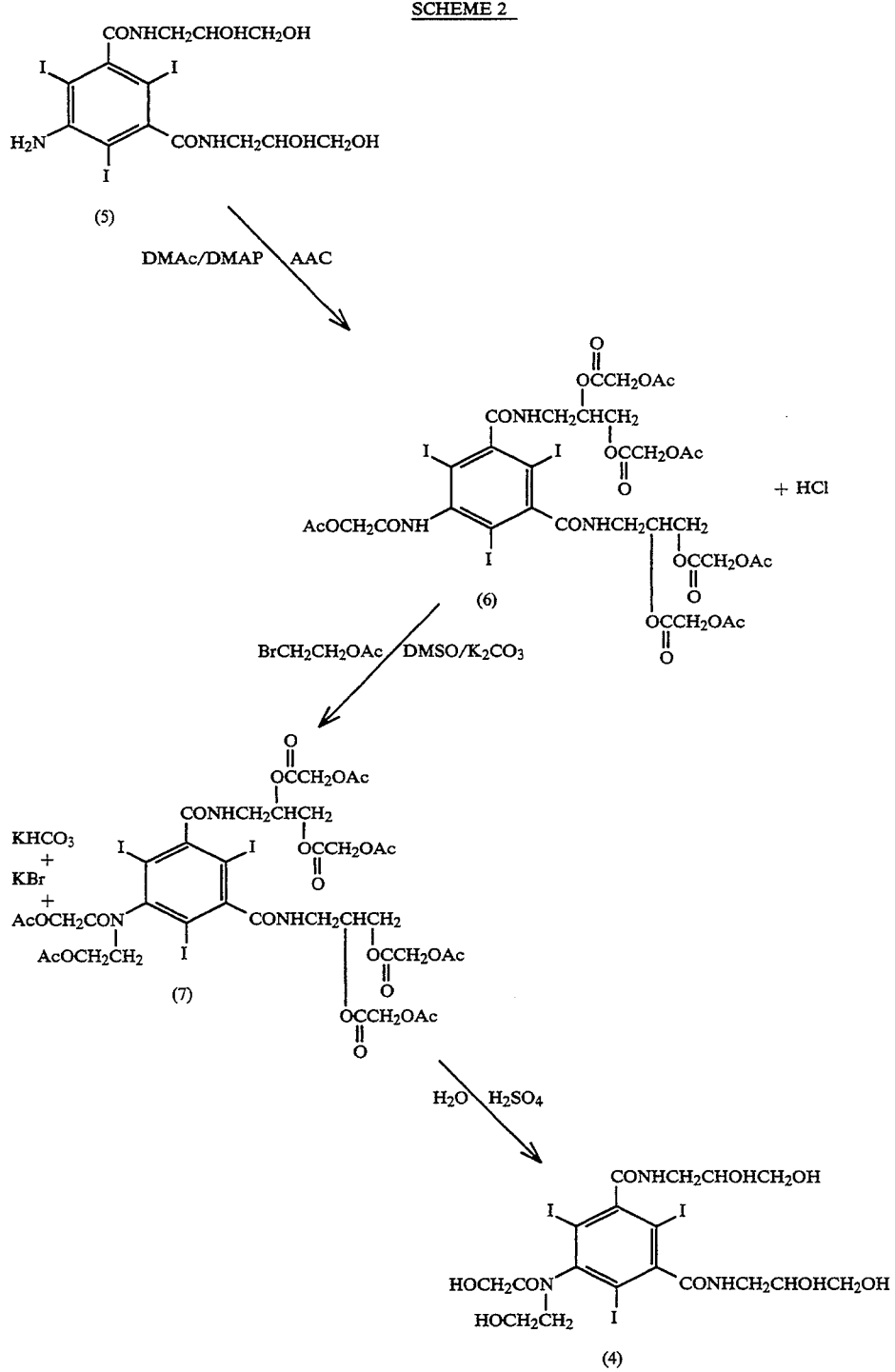

AAC = Acetoxyacetylchloride
DMAC = N,N-dimethylacetamide
DMAP = 4-dimethylaminopyridine
DMSO = Dimethylsulfoxide Both of the above-described processes, through an increase in the reaction solution concentration and an increase in temperature, have the advantage of eliminating the need for a 100% excess of acetoxyacetylchloride in the intermediate synthetic steps used in the production of N,N'-bis(2,3-dihydroxypropyl)-5-[N-(2 hydroxyethyl)glycolamido]-2,4,6-triiodoisophthalamide (ioversol). Elimination of the need for the 100% excess of acetoxyacetylchloride is important to reduce the costs of production and to provide alternative routes of production for N,N'-bis(2,3-dihydroxypropyl)-5-[N-(2-hydroxyethyl)glycolamido]-2,4,6-triiodoisophthalamide(4). Additionally, the need for acetic anhydride is likewise eliminated through the process illustrated in Scheme 2 which reduces the cost of production even further.

DETAILED DESCRIPTION OF THE INVENTION 5-acetoxyacetamido-N,N'-bis(2,3-diacetoxypropyl)-2,4,6-triiodoisophthalamide(2) may be prepared according to the present invention by first distilling off some of the solvents from 5-amino-N,N'-bis(2,3-diacetoxypropyl)-2,4,6triiodoisophthalamide(1) to reduce and/or remove any solvent impurities therefrom. This distillation of solvent(s) from compound 1 is optional. N,N-dimethylacetamide (DMAC) and a 7 to 36%, but preferably a 12%, excess of acetoxyacetychloride is then added to the previously distilled solution and stirred at preferably 50° C. until the acylation reaction is complete. The optimal temperature is within the range of 40° C. to 66° C., however, 50° C. was determined to be most preferable based on the experimental results illustrated in Table 1 below.

TABLE 1

| RUN # | Controlled Factors | | | Characteristic |
|---|---|---|---|---|
| | AAC | TEMP | GPML | AREA 1 |
| 1 | 1.570 | 40.00 | 0.670 | 49.30 |
| 2 | 1.570 | 40.00 | 0.670 | 52.00 |
| 3 | 1.570 | 60.00 | 0.670 | 74.00 |
| 4 | 1.570 | 41.00 | 0.400 | 18.00 |
| 5 | 1.570 | 40.00 | 1.000 | 66.90 |
| 6 | 1.570 | 40.00 | 1.000 | 65.00 |
| 7 | 1.050 | 50.00 | 1.000 | 70.10 |
| 8 | 1.100 | 50.00 | 1.000 | 69.40 |
| 9 | 1.110 | 51.00 | 1.250 | 84.20 |
| 10 | 2.230 | 51.00 | 1.250 | 97.70 |
| 11 | 1.110 | 62.00 | 1.520 | 83.40 |
| 12 | 1.670 | 62.00 | 1.520 | 93.40 |
| 13 | 1.050 | 40.00 | 1.670 | 66.20 |
| 14 | 1.050 | 50.00 | 1.670 | 90.30 |
| 15 | 2.000 | 40.00 | 1.280 | 80.50 |
| 16 | 0.970 | 54.00 | 1.940 | 87.00 |
| 17 | 1.220 | 50.00 | 1.190 | 86.80 |
| 18 | 1.050 | 50.00 | 1.620 | 88.90 |

The resulting solution after acylation is highly viscous and is therefore diluted to improve fluidity, and thereby ease workability. An organic solvent such as for example toluene, a halocarbon solvent or a chlorocarbon solvent is used for the dilution. Examples of such suitable solvents for dilution also include, but are not limited to carbon tetrachloride, dichloromethane, chloroform, 1,2-dichloroethane, 1,1,2-trichloroethylene, 1,1,2-dichloroethane, 1,1,1-trichloroethane and tetrachloroethylene, but preferably 1,1,2-trichloroethane.

After dilution, the solvent is extracted with aqueous sodium bicarbonate solution(s) (preferably containing approximately 10–15% sodium bicarbonate) and/or aqueous sodium chloride solutions (preferably containing approximately 10–15% sodium chloride) . This usually results in a mixture of 5-acetoxyacetamido-N,N'-bis(2,3-diacetoxypropyl) -2,4,6-triiodoisophthalamide(2) in 1,1,2-trichloroethane at approximately 25 to 30 percent solids. The resulting 5-acetoxyacetamido-N,N'-bis(2,3-diacetoxypropyl) -2,4,6-triiodoisophthalamide(2) may be used as an intermediate to produce N,N'-bis (2,3-dihydroxypropyl) -5-[N-(2-hydroxyethyl)glycolamido]-2,4,6-triiodoisophthalamide (ioversol) (4) as illustrated in Scheme 1 above. The production of N,N'-bis(2,3-dihydroxypropyl)-5-[N-(2-hydroxyethyl)glycolamido]-2,4,6-triiodoisophthalamide (ioversol) (4) from 5-amino-N,N'-bis(2,3-dihydroxypropyl)-2,4,6-triiodoisophthalamide(5) stirred with acetoxyacetylchloride (AAC) , N,N-dimethylacetamide (DMAC) and optionally 4-dimethylaminopyridine (DMAP) likewise may be used as an intermediate to produce ioversol as is illustrated in Scheme 2 above.

The present invention as described above is further illustrated by the following examples, but is not intended to be limited thereby.

EXAMPLE 1

The Preparation of 5-acetoxyacetamido-N,N'-bis-(2,3-diacetoxypropyl)-2,4,6-triiodoisophthalamide A solution of 5-amino-N,N'-bis(2,3-diacetoxypropyl)-2,4,6-triiodoisophthalamide (214.06 g) in 1,1,2-trichloroethane (TCE), i.e., approximately 200 g of 5-amino-N,N'-bis(2,3-diacetoxypropyl-2,4,6-triiodoisophthalamide in 14.06 g or 10 mL TCE, was prepared. N,N-dimethyl-acetamide (DMAC) 58.5 mL and 48.5 mL TCE were then added to the flask. The flask was heated to 50° C. and 35.03 g of AAC was added and the reaction was stirred until the reaction was complete.

The reaction mixture was then diluted with 1,1,2-trichloroethane (236 mL) and extracted with approximately 10% aqueous sodium bicarbonate (987 mL H2O: 98.7 g NaHCO3) and 10% aqueous sodium chloride (415 mL H2O: 41.5 g NaCl).

The resulting solution of 5-acetoxyacetamido-N,N'-bis(2,3-diacetoxypropyl)-2,4,6-triiodoisophthalamide (2) requires no further purification.

EXAMPLE 2

The Preparation of 5-acetoxyacetamido-N,N-bis[2,3-di(acetoxyacetoxypropyl)]-2,4,6-triiodoisophthalamide N,N-dimethylacetamide (75.2 ml), 4-dimethylaminopyridine (0.005 g moles, 0.61 g) and granular 5-amino-N,N-bis(2,3-dihydroxypropyl)-2,4,6-triiodoisophthalamide (0.1 g mole, 70.5 g) are placed into a 500 ml, 3-necked round bottomed flask. The mixture is stirred and heated to approximately 55° C. to dissolve the solids. Acetoxyacetylchloride (0.55 g mole, 7.45 g) is added slowly with stirring and the reaction temperature is controlled at 40°-66° C. After completing the addition, the reaction solution is allowed to stir at approximately 50° C. to complete the reaction, i.e., approximately three hours.

After the reaction is completed, 1,1,2-trichloroethane (TCE) is added (approximately 152 ml) diluting the solution by approximately a factor of 3 and the solution is stirred and cooled to approximately 20° C. Stirring and cooling are continued and aqueous sodium carbonate solution (approximately 0.6 moles, 52 g in a 13% w/v solution is slowly added to the stirred TCE solution at a rate which will maintain the temperature at less than 27° C. After stirring for 30 minutes, the reaction mixture containing TCE, DMAC, AAC, 5-amino-N,N-bis(2,3-dihydroxypropyl)-2,4,6-triiodoisophthalamide is transferred to a separatory funnel and the organic layer is separated from the aqueous layer. The organic layer is washed with a 10% w/v sodium chloride solution in a similar manner. The resulting TCE solution of the product is suitable for conversion to N,N-bis(2,3-dihydroxypropyl)-5-[N-(2-hydroxyethyl)glycolamido]-2,4,6-triiodoisophthalamide (ioversol) as shown in Scheme 2 above.

The process of the present invention is less expensive, easier to perform and results in the same or fewer impurities. Accordingly, having described our invention, we claim:

1. A process for the production of 5-acetoxyacetamido-N,N'-bis(2,3-diacetoxypropyl)-2,4,6-triiodoisophthalamide from 5-amino-N,N'-bis(2,3-diacetoxypropyl)-2,4,6-triiodoisophthalamide, comprising the steps of:
    (a) reacting N,N-dimethylacetamide, approximately 7–36% excess of acetoxyacetyl chloride, 5-amino-N,N'-bis(2,3-diacetoxypropyl)-2,4,6-triiodoisophthalamide, and an organic solvent under reaction forming conditions to form a reaction mixture; and
    (b) recovering 5-acetoxyacetamido-N,N'-bis-(2,3-diacetoxypropyl)-2,4,6-triiodoisophthalamide.

2. The process of claim 1 wherein said reaction mixture is diluted with an organic solvent prior to recovering 5-acetoxyacetamido-N,N'-bis-(2,3-diacetoxypropyl)-2,4,6-triiodoisophthalamide.

3. The process of claim 1 wherein said reaction mixture is diluted with an organic solvent and extracted with an aqueous solution prior to recovering 5-acetoxyacetamido-N,N'-bis-(2,3-diacetoxypropyl)-2,4,6-triiodoisophthalamide.

4. The process of claim 3, wherein said aqueous solution is an aqueous sodium bicarbonate solution.

5. The processed of claim 3, wherein said aqueous solution is an aqueous sodium chloride solution.

6. The process of claim 3, wherein said aqueous solution is an aqueous sodium bicarbonate followed by a sodium chloride solution.

7. The process of claim 1 wherein said reaction mixture is formed at a temperature within the range of 40° to 66° C.

8. The process of claim 1 wherein said reaction mixture is formed at a temperature of 50° C.

9. The process of claim 1 wherein said excess of acetoxyacetylchloride is 12%.

10. The process of claim 1 wherein a highly concentrated solution of said 5-amino-N,N'-bis-(2,3-diacetoxypropyl)-2,4,6-triiodoisophthalamide and said organic solvent is used to form said reaction mixture.

11. The process of claim 1 wherein one to three grams of said 5-amino-N,N'-bis(2,3-diacetoxypropyl)-2,4,6-triiodoisophthalamide plus up to five milliliters of said organic solvent are stirred to form a highly concentrated solution used to form said reaction mixture.

12. The process of claim 1, wherein 1.72 grams of said 5-amino-N,N'-bis(2,3-diacetoxypropyl)-2,4,6-triiodoisophthalamide plus one milliliter of said organic solvent are stirred to form a highly concentrated solution used to form said reaction mixture.

13. The process of claim 1, wherein said organic solvent may be the same or different selected from a group consisting, of carbontetrachloride, dichloromethane, chloroform, toluene, 1,2-dichloroethane, 1,1,2-trichloroethylene, 1,1,2-dichloroethane, 1,1,1-trichloroethane and tetrachloroethylene.

14. The process of claim 1, wherein said organic solvent is 1,1,2-trichloroethane.

15. The process of claim 1, wherein said 5-amino-N,N'-bis(2,3-diacetoxypropyl)-2,4,6-triiodoisophthalamide has solvent impurities reduced or removed therefrom by distilling off said solvent impurities.

16. A process for the production of a pentaacetate derivative of 5-acetoxyacetamido-N,N'-bis(2,3-diacetoxypropyl)-2,4,6-triiodoisophthalamide from 5-amino-N,N'-bis(2,3-diacetoxypropyl)-2,4,6-triiodoisophthalamide, comprising the steps of:
    (a) reacting N,N-dimethylacetamide, a 7 to 36% excess of acetoxyacetylchloride, 5-amino-N,N'-bis(2,3-dihydroxypropyl)-2,4,6-triiodoisophthalamide and an organic solvent under reaction forming conditions to form a reaction mixture; and
    (b) recovering the pentaacetate derivative of 5-acetoxyacetamido-N,N'-bis-[2,3-di(acetoxypropyl)]-2,4,6-triiodoisophthalamide.

17. The process of claim 16 wherein said reaction mixture is diluted with an organic solvent prior to recovering 5-acetoxyacetamido-N,N'-bis-(2,3-diacetoxypropyl)-2,4,6-triiodoisophthalamide.

18. The process of claim 16 wherein said reaction mixture is diluted with an organic solvent and extracted with an aqueous solvent prior to recovering 5-acetoxyacetamido-N,N'-bis-(2,3-diacetoxypropyl)-2,4,6-triiodoisophthalamide.

19. The process of claim 18, wherein said aqueous solution is an aqueous sodium chloride solution.

20. The process of claim 18, wherein said aqueous solution is an aqueous sodium bicarbonate solution.

21. The process of claim 18, wherein said aqueous solution is an aqueous sodium bicarbonate solution followed by a sodium chloride solution.

22. The process of claim 16 wherein said reaction mixture is formed at a temperature within the range of 40° C. to 60° C.

23. The process of claim 16 wherein said reaction mixture is formed at 50° C.

24. The process of claim 16 wherein said excess of acetoxyacetylchloride is 12%.

25. The process of claim 16 wherein a highly concentrated solution of said 5-amino-N,N'-bis-(2,3-diacetoxypropyl)-2,4,6-triiodoisophthalamide and said organic solvent is used to form said reaction mixture.

26. The process of claim 16 wherein one to three grams of said 5-amino-N,N'-bis(2,3-dihydroxypropyl)-2,4,6-triiodoisophthalamide plus up to five milliliters of said organic solvent are stirred to form a highly concentrated solution used to form said reaction mixture.

27. The process of claim 16, wherein 1.72 grams of said 5-amino-N,N'-bis(2,3-dihydroxypropyl)-2,4,6-triiodoisophthalamide plus one milliliter of said organic solvent are stirred to form a highly concentrated solution used to form said reaction mixture.

28. The process of claim 16, wherein said organic solvent may be the same or different selected from a group consisting of carbontetrachloride, dichloromethane, chloroform, toluene, 1,2-dichloroethane, 1,1,2-trichloroethylene, 1,1,2-dichloroethane, 1,1,1-trichloroethane and tetrachloroethylene.

29. The process of claim 16, wherein said organic solvent is 1,1,2-trichloroethane.

* * * * *